United States Patent
Kojima et al.

(10) Patent No.: US 10,214,568 B2
(45) Date of Patent: Feb. 26, 2019

(54) METHOD FOR PREPARING PHYCOCYANIN

(71) Applicants: EZAKI GLICO CO., LTD., Osaka (JP); GLICO NUTRITION CO., LTD., Osaka (JP)

(72) Inventors: Iwao Kojima, Osaka (JP); Koji Odan, Osaka (JP); Masahiro Nishikawa, Osaka (JP)

(73) Assignees: Ezaki Glico Co., Ltd., Osaka (JP); Glico Nutrition Co., Ltd., Osaka (JP)

( * ) Notice: Subject to any disclaimer, the term of this patent is extended or adjusted under 35 U.S.C. 154(b) by 132 days.

(21) Appl. No.: 14/370,603

(22) PCT Filed: Dec. 25, 2012

(86) PCT No.: PCT/JP2012/083471
§ 371 (c)(1),
(2) Date: Jul. 3, 2014

(87) PCT Pub. No.: WO2013/105430
PCT Pub. Date: Jul. 18, 2013

(65) Prior Publication Data
US 2014/0371433 A1  Dec. 18, 2014

(30) Foreign Application Priority Data
Jan. 12, 2012  (JP) ................. 2012-004013

(51) Int. Cl.
A61K 39/00 (2006.01)
C07K 14/195 (2006.01)
C09B 61/00 (2006.01)

(52) U.S. Cl.
CPC ............ C07K 14/195 (2013.01); C09B 61/00 (2013.01)

(58) Field of Classification Search
None
See application file for complete search history.

(56) References Cited

U.S. PATENT DOCUMENTS

2014/0314890 A1 *  10/2014  Gantar ................. A61K 35/748
424/780

FOREIGN PATENT DOCUMENTS

| CN | 1563083 A * | 1/2005 |
|---|---|---|
| CN | 101899102 | 12/2010 |
| IN | 746/DEL/2005 | 6/2009 |
| JP | 5-328938 | 12/1993 |
| JP | 6-16519 | 1/1994 |
| JP | 6-277075 | 10/1994 |
| JP | 7-310023 | 11/1995 |
| JP | 9-296124 | 11/1997 |
| JP | 2000-154333 | 6/2000 |
| JP | 2007-124912 | 5/2007 |
| JP | 4048420 | 12/2007 |
| JP | 2008-126168 | 6/2008 |
| JP | 2008-295365 | 12/2008 |
| JP | 4677250 | 2/2011 |

OTHER PUBLICATIONS

Definition of Spirulina from Wikipedia Sep. 30, 2015.*
Notification of Reasons for Refusal dated Oct. 25, 2016, in corresponding Japanese Application No. 2013-553241, with English Translation.
International Search Report dated Apr. 16, 2013, in International Application No. PCT/JP2012/083471.

* cited by examiner

*Primary Examiner* — Jana A Hines
*Assistant Examiner* — Khatol S Shahnan Shah
(74) *Attorney, Agent, or Firm* — Wenderoth, Lind & Ponack, L.L.P.

(57) ABSTRACT

Provided is a preparation method for phycocyanin, including: adding chitosan to a suspension of cyanobacteria containing phycocyanin; and filtering the suspension.

7 Claims, No Drawings

METHOD FOR PREPARING PHYCOCYANIN

TECHNICAL FIELD

The present invention relates to a preparation method for phycocyanin.

BACKGROUND ART

Cyanobacteria such as *Spirulina* contain phycocyanin and have been used as functional materials such as health foods, and food dyes.

As preparation methods for phycocyanin from cyanobacteria, there have been known methods disclosed in Patent Literatures 1 and 2.

The methods disclosed in Patent Literatures 1 and 2 involve using calcium phosphate as a flocculant. In the methods, however, filtration rates are very low, and purity is insufficient. Centrifugation may be carried out to remove impurities, but in the cases, the impurities cannot be removed satisfactorily.

A phycocyanin-containing solution after separation contains a high concentration of impurities and causes clogging. Therefore, a step of solid-liquid separation by filtration is difficult to be performed, and a step of sterilization using a filter cannot be integrated thereinto.

Phycocyanin is heat-labile and hence cannot be sterilized by heating or using a filter during the steps. Therefore, it has been necessary to immediately dry a product and then to sterilize the dried product.

CITATION LIST

Patent Literature

[PTL 1] JP 4677250 B2
[PTL 2] JP 4048420 B2

SUMMARY OF INVENTION

Technical Problem

An object of the present invention is to provide a technology for preparing phycocyanin contained in cyanobacteria with high efficiency and high purity.

Solution to Problem

The present invention provides the following preparation method for phycocyanin.
Item 1. A preparation method for phycocyanin, including: adding chitosan to a suspension of cyanobacteria containing phycocyanin; and filtering the suspension.
Item 2. A preparation method for phycocyanin according to Item 1, in which the concentration of the chitosan in the suspension to be filtered is from 0.01 to 1% by weight.
Item 3. A preparation method for phycocyanin according to Item 1 or 2, in which the suspension to be filtered includes a buffer.
Item 4. A preparation method for phycocyanin according to Item 3, in which the buffer is a phosphate buffer or an acetate buffer.
Item 5. A preparation method for phycocyanin according to any one of Items 1 to 4, including: adding chitosan and activated carbon to a suspension of cyanobacteria containing phycocyanin; and filtering the suspension.
Item 6. A preparation method for phycocyanin according to Item 5, in which the concentration of the chitosan in the suspension to be filtered is from 0.01 to 1% by weight and the concentration of the activated carbon in the suspension to be filtered is from 0.1 to 10% by weight.
Item 7. A preparation method for phycocyanin according to any one of Items 1 to 6, including simultaneously adding chitosan and activated carbon, followed by filtration.

Advantageous Effects of Invention

In production of a dried phycocyanin product or a liquid phycocyanin product, a high-quality phycocyanin dye containing a small amount of impurities was able to be produced. In addition, the ratio of the dye component collected was able to be improved. Further, in the case of production of the liquid product, a sterilized liquid product was able to be produced without needless steps of drying, sterilization, and re-dissolution.

When chitosan was used as a flocculant to be used for a flocculation step in production steps in an optimum blending amount, phycocyanin was able to be separated from residues of cyanobacteria by filtration while the filtration rate was kept at a satisfactory level.

Improvement of the flocculation step was able to remove impurities (such as nucleic acid components) causing clogging in a membrane. Therefore, a sterilization step was able to be integrated into the subsequent step to sterilize a phycocyanin-containing solution. Sterilization was achieved at an early stage in the production steps, and hence reduction in quality due to contamination during the production steps was able to be avoided. Further, it was not necessary to dry the product, and easy production of a liquid product (which accounts for most of the current commercially available products) was achieved by omitting needless steps. Further, in the production of a liquid product, in the related art, it was necessary to add an antifoaming agent (containing a fatty acid ester or the like as a major component) to prevent excessive foaming in re-dissolving a dried product in water. However, according to the present invention, it was possible to produce a liquid product without adding the antifoaming agent.

Further, in the chitosan flocculation step, when chitosan was used in combination with activated carbon to promote an effect of removing impurities, it was possible to significantly improve filtration efficiency and to reduce the burden of washing of a filtration cloth or a microfiltration membrane to be used in actual production.

DESCRIPTION OF EMBODIMENTS

In the present invention, examples of the cyanobacteria include cyanobacteria belonging to the genera *Spirulina, Arthrospira, Aphanizomenon, Fisherella, Anabaena, Nostoc, Synechocystis, Synechococcus, Tolypothrix, Aphanothece, Mastigoclaus, Pleurocapsa*. Of those, cyanobacteria belonging to the genera *Spirulina* and *Arthrospira* are preferred because the bacteria are produced in an industrial scale and have been confirmed to be safe.

As raw materials for preparation of phycocyanin, there may be used raw cyanobacteria or dried cyanobacteria. The dried product of the cyanobacteria may be obtained from raw cyanobacteria by a conventional method or may be a commercially available dried product.

In the method of the present invention, a suspension of cyanobacteria is prepared. For example, in the case of using the dried product of the cyanobacteria, a suspension containing from 0.1 to 20% by weight of the cyanobacteria in terms of a solid content (dried product) may be prepared. In the case of using the raw cyanobacteria, a suspension may be prepared so that the solid content falls within such range.

The suspension of the cyanobacteria is obtained by suspending the cyanobacteria in water. The suspension may be formed of water and the cyanobacteria, but in order to adjust the pH, the cyanobacteria may be suspended in a buffer. The buffer preferably includes, but is not limited to, a phosphate buffer and an acetate buffer. The pH of the suspension is, for example, from about 4 to 8, preferably from about 5 to 7. A salt to be used for maintaining the pH may be added as a solid or as an aqueous solution to the cyanobacteria or the suspension thereof. The salt of the buffer (buffering agent) is not particularly limited, and is preferably a phosphate, an acetate, or a citrate, more preferably a phosphate or an acetate. In the case where the kind of the salt is a phosphate, the phosphate may be added as a solution or as a solid to the suspension.

Examples of the phosphate include: a sodium phosphate such as trisodium phosphate, sodium dihydrogen phosphate, or disodium hydrogen phosphate; a potassium phosphate such as tripotassium phosphate, potassium dihydrogen phosphate, or dipotassium hydrogen phosphate; and a water-soluble phosphate such as ammonium dihydrogen phosphate. The phosphate buffer is preferably a buffer of phosphoric acid and an alkali metal (such as sodium, potassium, or lithium), and examples thereof include a buffer of sodium dihydrogen phosphate and disodium hydrogen phosphate and a buffer of potassium dihydrogen phosphate and dipotassium hydrogen phosphate. The phosphate buffer may be prepared using any other materials such as trisodium phosphate and phosphoric acid. The phosphate buffer is preferably a buffer of sodium dihydrogen phosphate and disodium hydrogen phosphate.

An example of the acetate is a water-soluble acetate such as sodium acetate, potassium acetate, lithium acetate, or ammonium acetate. The acetate buffer is preferably includes a buffer of acetic acid and an alkali metal (such as sodium, potassium, or lithium), and examples thereof include a buffer of acetic acid and sodium acetate and a buffer of acetic acid and potassium acetate. The acetate buffer may be prepared using any other raw materials such as calcium acetate or magnesium acetate and acetic acid.

Examples of the citrate include: a sodium citrate such as sodium dihydrogen citrate, disodium hydrogen citrate, or trisodium citrate; a potassium citrate such as potassium dihydrogen citrate, dipotassium hydrogen citrate, or tripotassium citrate; ammonium dihydrogen citrate; and other water-soluble citrates. The citrate buffer is preferably a buffer of citric acid and an alkali metal (such as sodium, potassium, or lithium), and examples thereof include a buffer of sodium dihydrogen citrate and disodium hydrogen citrate, a buffer of potassium dihydrogen citrate and dipotassium hydrogen citrate, and a buffer of citric acid and trisodium citrate. The citrate buffer may be prepared using any other materials such as calcium citrate and citric acid.

The buffer is added so that the concentration of the buffering agent in the suspension is preferably from 0.1 to 10% by weight, more preferably from 0.3 to 3% by weight.

For example, the phosphate buffer is added so that the concentration of phosphoric acid+phosphate in the suspension is preferably from 0.1 to 10% by weight, more preferably from 0.3 to 3% by weight.

The acetate buffer is added so that the concentration of acetic acid+acetate in the suspension is preferably from 0.1 to 10% by weight, more preferably from 0.3 to 3% by weight.

The citrate buffer is added so that the concentration of citric acid+citrate in the suspension is preferably from 0.1 to 10% by weight, more preferably from 0.1 to 1% by weight.

Chitosan is added to the suspension of the cyanobacteria. Chitosan can effectively adsorb impurities derived from the cyanobacteria and the impurities can be removed by filtration. Addition of chitosan can drastically improve the filtration rate. The blending amount of chitosan in the suspension is, for example, from about 0.01 to 1% by weight, preferably from about 0.03 to 0.8% by weight, more preferably from about 0.05 to 0.5% by weight. When the blending amount of chitosan is too small, the filtration rate decreases owing to clogging, and when the blending amount of chitosan is too large, the filtration rate decreases. That is, there is an optimum blending amount of chitosan.

The optimum concentration of chitosan in the phosphate buffer is different from that in the acetate buffer. In the case of using the acetate buffer, the blending amount of chitosan is preferably from about 0.05 to 0.3% by weight, while in the case of using the citrate buffer, the blending amount of chitosan is preferably from about 0.1 to 0.6% by weight.

In addition, the optimum concentration of chitosan depends on the concentration of the buffer. That is, when the concentration of the buffer becomes higher, the blending amount of chitosan is preferably raised, and when the concentration of the buffer becomes lower, the blending amount of chitosan is preferably reduced.

In a preferred embodiment, chitosan and activated carbon are added to the suspension of the cyanobacteria, and the suspension is filtered. The order of addition of chitosan and activated carbon is not particularly limited. Activated carbon may be added after addition of chitosan, chitosan may be added after addition of activated carbon, or chitosan and activated carbon may be added simultaneously. Filtration is preferably carried out in the presence of chitosan and activated carbon. The blending amount of activated carbon is not particularly limited, and is preferably from about 0.05 to 5% by weight, more preferably from about 0.1 to 2% by weight.

In a preferred embodiment, filtration is carried out after simultaneous addition of chitosan and activated carbon. The term "simultaneous" as used herein refers to a state in which components are present in the same solution, and the order and timing of addition are not limited.

The temperature of the water suspension in preparation and filtration of the suspension is preferably from about 5 to 50° C., more preferably from about 10 to 35° C.

In preparation of a solution of a phycocyanin dye, the water suspension may be subjected to ultrasonic treatment or stirring treatment. Stirring may be carried out very slowly, or the stirring rate may be raised as long as no excessive foaming occurs in the suspension. In addition, stirring may be carried out intermittently. Chitosan and, if necessary, activated carbon are added, and the suspension is stirred for a predetermined period of time and filtered. The time for stirring or the like is, for example, from 1 minute to 24 hours, preferably from about 15 minutes to 5 hours. After uniform mixing of chitosan and activated carbon in the suspension, the suspension is filtered. The suspension may be stirred or may be allowed to stand still up to completion of the filtration. The time for completion of the filtration is, for example, from 1 minute to 64 hours, preferably from about 3 minutes to 24 hours.

The thus-prepared phycocyanin may be used as a solution (filtrate) or may further be concentrated. As a concentration method, concentration by ultrafiltration is preferably employed because the method can decrease the contents of low-molecular-weight dyes, organic impurities, and inorganic ions contained in a solution to improve a purification degree. An ultrafiltration membrane to be used for the ultrafiltration has a molecular weight cut off of preferably from 1,000 to 30,000, more preferably from 5,000 to 20,000.

Sterilization is preferably carried out using a membrane filter (MF membrane) because dyes are decomposed by heating the phycocyanin solution. When chitosan and activated carbon are used, components that may cause clogging are removed. Therefore, filtration can be carried out using a membrane filter without difficulty.

Phycocyanin obtained by the preparation method of the present invention may be provided as an aqueous solution obtained by stabilizing the solution with a sugar (such as trehalose or glycerin), a salt (for example, a citrate), or the like, or as dry powder obtained by subjecting the solution to a drying step. Any drying method may be employed as long as phycocyanin is not denatured or deteriorated, and the method is preferably spray drying, reduced-pressure drying, or freeze drying.

The term "chitosan" as used herein refers to a compound that is obtained by deacetylating chitin forming exoskeleton of crustacea such as crab and shrimp together with inorganic substances (calcium compounds) and dissolves in an acidic aqueous solution. The chemical structure of chitosan is characterized by including glucosamine obtained by deacetylating chitin and having many amino structures in its molecule.

The "activated carbon" to be used in the present invention is not particularly limited, and all commercially available activated carbons may be used widely. The activated carbon may have a powdery form or a granular form. As raw materials for the activated carbon, there may be given, for example: plant (such as coconut husk, palm, fruit seeds, sawdust, eucalyptus, and pine)-based, coal-based, and petroleum-based cokes, and carbonized pitch prepared using them as raw materials; phenol resins; vinyl chloride resins; and vinylidene chloride resins. Of those, activated carbons prepared using the plant-based raw materials such as coconut husk, palm, fruit seeds, sawdust, eucalyptus, and pine are preferably used. The activated carbon suitably has a specific surface area of, for example, from about 500 to 3,000 $m^2/g$, preferably from about 800 to 2,500 $m^2/g$.

Chitosan to be used in the present invention preferably contains impurities as less as possible. The content of the impurities is preferably about 10% by weight or less, more preferably about 5% by weight or less, even more preferably about 1% by weight or less.

Chitosan to be used in the present invention may be used as an aqueous solution or may be dissolved in a solvent other than water before use. Alternatively, chitosan may be added as powder or as solid directly to the suspension of the cyanobacteria without dissolving it in water or a solvent.

EXAMPLES

Hereinafter, the present invention is described in more detail by way of Examples.
(Used Flocculant)
Polyaluminum Chloride (PAC; cationic polymer flocculant)
Product name: TAIPAC (manufactured by TAIMEI CHEMICALS Co., Ltd.)
Dimethylaminoethyl methacrylate methyl chloride salt homopolymer (Cationic polymer flocculant)
Product name: TAIPOLYMER TC-580 (manufactured by TAIMEI CHEMICALS Co., Ltd.)
Acrylamide-Sodium Acrylate Copolymer (anionic polymer flocculant)
Product name: TAIPOLYMER TA945 (manufactured by TAIMEI CHEMICALS Co., Ltd.)
Chitin and chitosan (cationic polymer flocculants)
Activated carbon
Product name: Fuji Activated Carbon Flower F1-W50 (manufactured by SERACHEM Co., Ltd.)

Example 1

(Method)

Dried *Spirulina* cells were suspended in a solution of sodium phosphate (0.82% sodium dihydrogen phosphate+ 0.84% disodium hydrogen phosphate), and the suspension was stirred slowly at 20° C. for 16 hours to extract a phycocyanin component. A variety of flocculants were added to the extract, and the extract was filtered (100-ml scale) using filter paper. Then, the amount of the filtrate collected for the first one minute was measured, and the filtrate was analyzed. Phycocyanin has an absorption peak of A618 nm, and an A260 nm (absorption maximum of a nucleic acid) value with respect to the A618 value was calculated as an indicator of impurities. A residual ratio of color (collection rate in a filtration step) was represented as a relative value with respect to an A618 value of an untreated filtrate (filtrate not subjected to flocculant treatment).

(Results)

As shown in Tables 1 and 2, in the case of the chitosan treatment, the filtration rate was the highest, and the ratio of impurities in the filtrate was the lowest. In the case of the chitosan treatment, the residual ratio of color was the highest. Further, in the case of the chitosan treatment, the amount of the filtrate having passed through a filter for sterilization was the largest.

TABLE 1

| | Filtration rate (ml) | Degree of impurities A260/A618 | Residual ratio of color (%) |
|---|---|---|---|
| Untreated | 0.2 | 1.58 | 100.0 |
| Treated with calcium phosphate (1% $CaCl_2$) | 7.5 | 1.57 | 81.2 |
| Treated with chitosan (0.4% FLONAC C) | 27.0 | 1.09 | 100.5 |
| PAC (0.2% in terms of $Al_2O_3$) | 0.0 | 1.28 | 64.9 |
| TC580 (0.1%) | 3.0 | 1.22 | 84.3 |
| TA945 (0.02%) | 1.5 | 1.48 | 91.5 |

TABLE 2

| | | Filtration rate* (ml/min) | Impurities A260/A618 | Residual ratio of dye (%) | Amount of filtration having passed through filter** (ml) |
|---|---|---|---|---|---|
| Treated with chitosan | Untreated | 0.0 | 2.54 | 100.2 | 0.8 |
| | Treated with 0.075% FLONAC C | 0.0 | 1.38 | 98.2 | 8.2 |
| | Treated with 0.15% FLONAC C | 1.0 | 1.34 | 98.8 | 10.5 |
| | Treated with 0.225% FLONAC C | 3.0 | 1.27 | 96.5 | 20.0 |
| | Treated with 0.3% FLONAC C | 9.0 | 1.19 | 92.6 | 25.0 |
| | Treated with 0.375% FLONAC C | 11.5 | 1.18 | 91.8 | 52.0 |
| | Treated with 0.4% FLONAC C | 27.0 | 1.09 | 100.5 | 68.0 |
| | Treated with 0.6% FLONAC C | 7.5 | 1.68 | 100 | 60.0 |
| Treated with calcium phosphate | Treated with 0.97% $CaCl_2$ | 0.0 | 1.97 | 90 | 1.5 |
| | Treated with 1.00% $CaCl_2$ | 7.5 | 1.57 | 81.2 | 1.8 |
| | Treated with 1.75% $CaCl_2$ | 7.5 | 1.56 | 80 | 2.0 |
| Polymer flocculant | Treated with PAC (0.2% in terms of $Al_2O_3$) | 0.0 | 1.28 | 64.9 | 0.0 |
| | Treated with TC580 (0.1%) | 3.0 | 1.22 | 84.3 | 1.1 |
| | Treated with TA945 (0.02%) | 1.5 | 1.48 | 91.5 | 0.0 |

*Amount of a filtrate obtained for the first one minute when 100 ml of each treated extract are allowed to pass through filter paper (No. 2, 185 mm, manufactured by ADVANTEC) folded in four.
**Total amount of a filtrate having passed through a filter for sterilization (pour size: 0.2 μm, membrane area: about 7.5 cm²).

In the resultant phycocyanin solutions, the maximum absorption values of impurities such as nucleic acids determined at about 260 nm were significantly reduced as compared to the conventional methods involving treatment with no flocculant, treatment with calcium phosphate, etc. suggesting that the dye solutions of the present invention contained almost no impurities derived from *Spirulina*.

Example 2

(Method)

Dried *Spirulina* cells were suspended in solutions of sodium phosphate (solutions having the same weight ratio between sodium dihydrogen phosphate and disodium hydrogen phosphate and different concentrations of sodium dihydrogen phosphate and disodium hydrogen phosphate), or a mixed solution of sodium acetate and acetic acid, and the suspension was stirred slowly at 20° C. for 16 hours to extract a phycocyanin component. Chitosan (FLONAC C) was added to the extract, and the extract was filtered (100-ml scale) using filter paper. Then, the amount of the filtrate collected for the first one minute was measured, and the filtrate was analyzed. Phycocyanin has an absorption peak of A618 nm, and an A260 nm (absorption maximum of a nucleic acid) value with respect to the A618 value was calculated as an indicator of impurities. A residual ratio of color (collection ratio in a filtration step) was represented as a relative value with respect to an A618 value of an untreated filtrate (filtrate not subjected to flocculant treatment).

(Results)

As shown in Table 3, in all the cases where the dried *Spirulina* cells were suspended in tap water (salt concentration: 0%), the phosphate buffers having different concentrations, or the acetate buffer, filtration was able to be carried out at satisfactory filtration rates owing to the chitosan treatment, and the ratios of impurities in the filtrates were low. In addition, the filtrates having passed through the filter for sterilization were obtained in sufficient amounts.

TABLE 3

| Buffer | Chitosan treatment | Filtration rate (ml/min) | A260/A618 | Residual ratio of dye (%) | Amount of filtrate having passed through filter (ml) |
|---|---|---|---|---|---|
| Salt concentration 0% | Treated with 0.18% FLONAC C | 16.7 | 1.17 | 95.0 | 35.0 |
| 0.43% sodium dihydrogen phosphate + 0.44% disodium hydrogen phosphate | Treated with 0.18% FLONAC C | 21.0 | 1.34 | 98.2 | 70.0 |
| 0.645% sodium dihydrogen phosphate + 0.66% disodium hydrogen phosphate | Treated with 0.30% FLONAC C | 19.6 | 1.36 | 95.8 | 65.0 |

TABLE 3-continued

| Buffer | Chitosan treatment | Filtration rate (ml/min) | A260/ A618 | Residual ratio of dye (%) | Amount of filtrate having passed through filter (ml) |
|---|---|---|---|---|---|
| 0.82% sodium dihydrogen phosphate + 0.84% disodium hydrogen phosphate | Treated with 0.4% FLONAC C | 27.0 | 1.09 | 100.5 | 68.0 |
| 1.29% sodium dihydrogen phosphate + 1.32% disodium hydrogen phosphate | Treated with 0.45% FLONAC C | 19.5 | 1.28 | 92.6 | 43.0 |
| 1.5% sodium acetate trihydrate + 0.12% acetic acid | Extract treated with 0.15% FLONAC C | 27.7 | 1.18 | 91.8 | 52.0 |

Example 3 and Comparative Example 1

Preparation of phycocyanin was carried out in accordance with the following protocol by centrifugation (Comparative Example 1) or by filtration (Example 3).
(i) Extraction: *Spirulina* powder is dispersed at 3% in a phosphate buffer (0.86% sodium dihydrogen phosphate+ 0.88% disodium hydrogen phosphate), and is subjected to extraction with stirring for 15 h.
(ii) Flocculation: Water-soluble chitosan is added at 0.3% to the extract to perform flocculation.
(iii) Solid-liquid separation:
The resultant is filtered with filter paper, and the filtrate is collected.
The resultant is centrifuged under a centrifugation condition of from 440 to 10,000×g for 10 min, and the supernatant is collected.
(iv) Analysis: Each collected liquid is measured for the amount of the filtrate having passed through a 0.45-µm membrane filter. Filter paper: ADVANTEC No. 2 qualitative filter paper is used. Centrifuge: Hitachi SCR20B and an angle rotor (50E-6A) are used.
Table 4 below shows the results.

TABLE 4

| | Solid-liquid separation | Amount of liquid collected (ml) | Amount of filtrate having passed through 0.45-µm filter (ml) |
|---|---|---|---|
| Example 3 | No. 2 filtration | 88 | 33 |
| Comparative Example 1 | 2,000 rpm (440 × g) | 80 | 14 |
| | 6,000 rpm (3,700 × g) | 83 | 23 |
| | 10,000 rpm (10,000 × g) | 85 | 23 |

The phycocyanin solution prepared by filtration provided a large amount of the filtrate having passed through the 0.45-µm membrane filter as compared to the phycocyanin solutions prepared by centrifugation. The results revealed that the solution prepared by filtration contained a smaller amount of impurities causing clogging.

The results show that, according to the present invention, it is possible to reduce the burden on the membrane used in the microfiltration step after filtration in actual production and eliminate a membrane regenerating step for removing clogging.

This shows that, in preparation of phycocyanin using chitosan, filtration is superior to centrifugation.

Example 4

Preparation of phycocyanin was carried out in accordance with the following protocol by "simultaneous treatment with chitosan and activated carbon" or by "separate treatment with chitosan and activated carbon."
Separate treatment process: "extraction"→ "flocculation (chitosan) treatment"→"filtration"→"activated carbon treatment"→"filtration"
Simultaneous treatment process: "extraction"→ "chitosan+ activated carbon treatment"→"filtration"
(i) Extraction: *Spirulina* powder is dispersed at 3% in a phosphate buffer (0.86% sodium dihydrogen phosphate+ 0.88% disodium hydrogen phosphate), and is subjected to extraction with stirring for 15 h.
(ii) Chitosan treatment: Water-soluble chitosan is added at 0.4% to the extract to perform flocculation.
(iii) Activated carbon treatment: Activated carbon is added at 0.5% to the extract, and the resultant is stirred for 1 h.
(iv) Filtration: The resultant is filtered with filter paper, and the filtrate is collected.
(v) Analysis: Each collected liquid is measured for the amount of the filtrate having passed through a 0.45-µm membrane filter.
Table 5 shows the results.

TABLE 5

| | Amount of liquid collected (ml) | Amount of filtrate having passed through 0.45-µm filter (ml) |
|---|---|---|
| No treatment | | 3 |
| Separate treatment | 76 | 49 |
| Simultaneous treatment | 87 | 85 or more |

The amount of the filtrate having passed through the 0.45-µm membrane filter in the simultaneous treatment process was larger than that in the separate treatment process. This revealed that the filtrate obtained by the simultaneous treatment process contained a smaller amount of impurities causing clogging.

When the simultaneous treatment with chitosan and activated carbon is carried out, it is possible to reduce the burden on the membrane used in the microfiltration step after filtration in actual production and eliminate a membrane regenerating step for removing clogging.

This shows that, in preparation of phycocyanin using chitosan and activated carbon, the simultaneous treatment process is superior to the separate treatment process.

Example 5 and Comparative Example 2

Preparation of phycocyanin by simultaneous treatment with chitosan and activated carbon was carried out in accordance with the following protocol by centrifugation (Comparative Example 2) or by filtration (Example 5).
(i) Extraction: *Spirulina* powder is dispersed at 3% in a phosphate buffer (0.86% sodium dihydrogen phosphate+ 0.88% disodium hydrogen phosphate), and is subjected to extraction with stirring for 15 h.
(ii) Flocculation: Water-soluble chitosan is added at 0.3% to the extract to perform flocculation.
: activated carbon treatment: activated carbon is added at 0.5% to the extract, and the resultant is slowly stirred for 1 h.
(iii) Solid-liquid separation:
The resultant is filtered with filter paper, and the filtrate is collected.
The resultant is centrifuged under a centrifugation condition of 10,000×g for 10 min, and the supernatant is collected.
(v) Analysis: Each collected liquid is measured for the amount of the filtrate having passed through a 0.45-μm membrane filter. Filter paper: ADVANTEC No. 2 qualitative filter paper is used. Centrifuge: Hitachi SCR20B and an angle rotor (50F-6A) are used.
Table 6 shows the results.

TABLE 6

|  | Amount of liquid collected (ml) | Amount of filtrate having passed through 0.45-μm filter (ml) |
|---|---|---|
| Simultaneous treatment, filtration | 170 | 170 |
| Simultaneous treatment, centrifugation | 188 | 70 |

The amount of the filtrate having passed through the 0.45-μm filter, obtained by the simultaneous treatment and filtration, was significantly larger than that obtained by the simultaneous treatment and centrifugation.

The results shown in Table 6 suggest that, when phycocyanin is prepared by employing the simultaneous treatment with chitosan and activated carbon, and the filtration in place of the centrifugation, it is possible to remove impurities causing clogging in the 0.45-μm membrane.

INDUSTRIAL APPLICABILITY

In the preparation method for phycocyanin according to the present invention, it is possible to prepare phycocyanin rapidly with high purity from a suspension of cyanobacteria and to remove residues of the cyanobacteria, unnecessary proteins, nucleic acids in a very efficient manner. Further, according to the present invention, it is possible to remove, before the microfiltration step, impurities that cannot pass through a microfilter and cause troubles in conventional preparation methods for phycocyanin by flocculation filtration based a reaction of calcium phosphate or centrifugation, resulting in producing a liquid phycocyanin product. In addition, when activated carbon is used in combination in flocculation, it can be expected to reduce the work load of the steps in actual production as mentioned below.

(Filtration Step)

The amount of the filtrate collected increases because compression of the cake can be achieved sufficiently.

The amount of a liquid that can be treated significantly increases because clogging is hard to occur in a filter cloth for a filter press or the like.

The filter cloth can be easily washed after use.

The cake can be readily separated from the cloth. Further, automatic operation control can be carried out using a fully automatic press filtration machine.

(Microfiltration Step)

The filtration rate of the microfilter increases, resulting in a significant increase in the amount of a liquid that can be treated.

Clogging in the membrane is significantly reduced, resulting in facilitating washing (regeneration).

The invention claimed is:

1. A preparation method for phycocyanin, comprising: simultaneously adding chitosan and activated carbon to a suspension of cyanobacteria containing phycocyanin to form a flocculent; and filtering the flocculent using a filter, wherein the suspension to be filtered comprises tap water or a buffer, and wherein the concentration of the chitosan in the suspension to be filtered is from 0.01 to 1% by weight and wherein the weight ratio of chitosan:cyanobacteria is from 0.375:3 to 0.6:3.

2. The preparation method for phycocyanin according to claim 1, wherein the suspension to be filtered comprises a buffer.

3. The preparation method for phycocyanin according to claim 2, wherein the buffer is a phosphate buffer or an acetate buffer.

4. The preparation method for phycocyanin according to claim 1, in which the concentration of the activated carbon in the suspension to be filtered is from 0.1 to 10% by weight.

5. The preparation method for phycocyanin according to claim 1, wherein a concentration of the chitosan in the suspension to be filtered is from 0.075 to 0.8% by weight.

6. The preparation method for phycocyanin accordingly to claim 1, wherein a concentration of the chitosan in the suspension to be filtered is from 0.075 to 0.8% by weight and a concentration of the activated carbon in the suspension to be filtered is from 0.1 to 10% by weight.

7. The preparation method for phycocyanin according to claim 1, wherein the filter is a filter paper or a filter cloth.

* * * * *